US00PP35294P2

(12) United States Plant Patent
Lommerse et al.

(10) Patent No.: US PP35,294 P2
(45) Date of Patent: Aug. 1, 2023

(54) ***BETONICA* PLANT NAMED 'SUMMER SNOWCONE'**

(50) Latin Name: *Betonica officinalis*
Varietal Denomination: Summer Snowcone

(71) Applicant: FUTURE PLANTS LICENTIE B.V., Hillegom (NL)

(72) Inventors: Gerardus Adrianus Petronella Lommerse, Noordwijkerhout (NL); Hendrikus Petrus Lommerse, Lisse (NL)

(73) Assignee: FUTURE PLANTS LICENTIE B.V., Hillegom (NL)

( * ) Notice: Subject to any disclaimer, the term of this patent is extended or adjusted under 35 U.S.C. 154(b) by 0 days.

(21) Appl. No.: 17/983,670

(22) Filed: Nov. 9, 2022

(51) Int. Cl.
*A01H 5/02* (2018.01)
*A01H 6/50* (2018.01)

(52) U.S. Cl.
USPC ..... Plt./263.1

(58) Field of Classification Search
USPC ..... Plt./263.1
CPC ..... A01H 5/02; A01H 6/50
See application file for complete search history.

(56) References Cited

U.S. PATENT DOCUMENTS

PP21,436 P2 * 11/2010 Hawke ..... A01H 5/02
Plt./263.1

OTHER PUBLICATIONS

Cpvo Register 4.3.55, retrieved on Feb. 1, 2023 at https://online.plantvarieties.eu/publicConsultationDetails?registerId=20222027&denomination=summer%20snowcone, 3 pp. (Year: 2023).*

* cited by examiner

*Primary Examiner* — June Hwu
(74) *Attorney, Agent, or Firm* — C. Anne Whealy

(57) ABSTRACT

A new and distinct cultivar of *Betonica* plant named 'Summer Snowcone', characterized by its relatively compact and broadly upright plant habit; moderately vigorous to vigorous growth habit; dark green-colored leaves; freely flowering habit; relatively long inflorescences with white-colored flowers; and good garden performance.

2 Drawing Sheets

Figure 1:
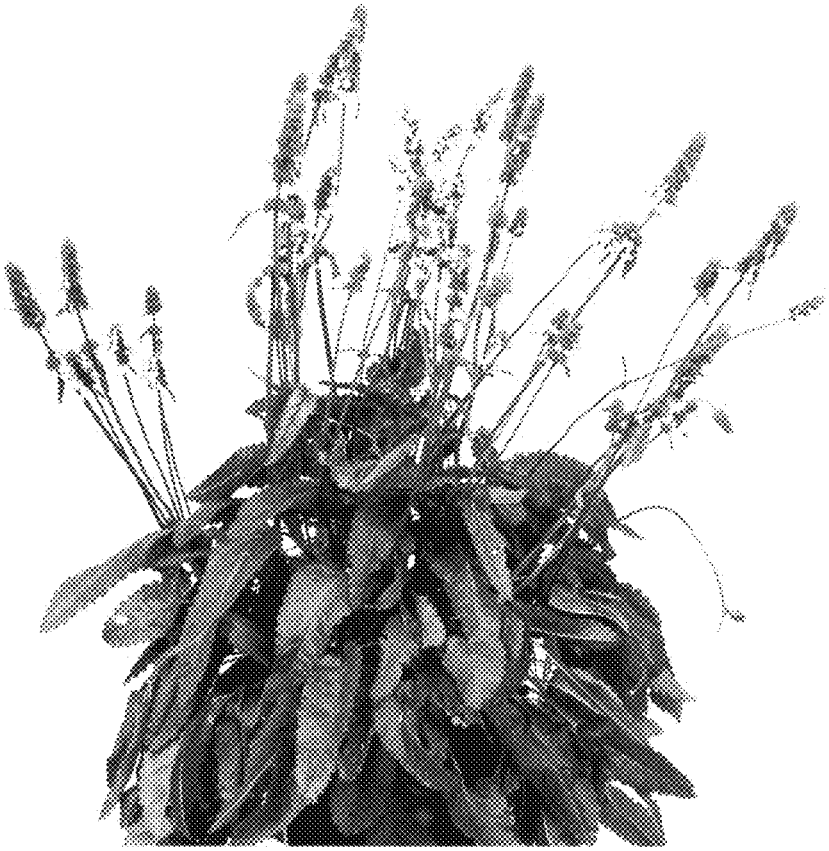

Botanical designation: *Betonica officinalis*.
Cultivar denomination: 'SUMMER SNOWCONE'.

BACKGROUND OF THE INVENTION

The present invention relates to a new and distinct cultivar of *Betonica* plant, botanically known as *Betonica officinalis*, previously classified as *Stachys officinalis* and *Stachys betonica*, and hereinafter referred to by the name 'Summer Snowcone'.

The new *Betonica* plant is a product of a planned breeding program conducted by the Inventors in Lisserbroek, The Netherlands. The objective of the breeding program was to create new compact and freely-flowering *Betonica* plants with unique and attractive flower colors.

The new *Betonica* plant originated from an open-pollination in June, 2016 in Lisserbroek, The Netherlands, of *Betonica officinalis* 'Alba', not patented, as the female, or seed, parent with an unknown selection of *Betonica officinalis* as the male, or pollen, parent. The new *Betonica* plant was discovered and selected by the Inventors as a single plant from within the progeny of the stated open-pollination in a controlled environment in Lisserbroek, The Netherlands in June, 2017.

Asexual reproduction of the new *Betonica* plant by divisions in a controlled environment in Lisserbroek, The Netherlands since August, 2017 has shown that the unique features of this new *Betonica* plant are stable and reproduced true to type in successive generations.

SUMMARY OF THE INVENTION

Plants of the new *Betonica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Summer Snowcone'. These characteristics in combination distinguish 'Summer Snowcone' as a new and distinct *Betonica* plant:

1. Relatively compact and broadly upright plant habit.
2. Moderately vigorous to vigorous growth habit.
3. Dark green-colored leaves.
4. Freely flowering habit.
5. Relatively long inflorescences with white-colored flowers.
6. Good garden performance.

Plants of the new *Betonica* differ primarily from plants of the female parent, 'Alba', in plant habit as plants of the new *Betonica* are more compact than and shorter than plants of 'Alba'. In addition, plants of the new *Betonica* are more freely flowering than plants of 'Alba'.

Plants of the new *Betonica* can be compared to plants of *Betonica officinalis* 'Ukkie', not patented. Plants of the new *Betonica* and 'Ukkie' differ primarily in the following characteristics:

1. Plants of the new *Betonica* have stronger stems than plants of 'Ukkie'.
2. Plants of the new *Betonica* have darker green-colored leaves than plants of 'Ukkie'.
3. Plants of the new *Betonica* have longer inflorescences than plants of 'Ukkie'.
4. Plants of the new *Betonica* have white-colored flowers whereas plants of 'Ukkie' have lilac purple-colored flowers.

Plants of the new *Betonica* can also be compared to plants of *Betonica officinalis* 'Pink Cotton Candy', disclosed in U.S. Plant Pat. No. 21,436. Plants of the new *Betonica* and 'Pink Cotton Candy' differ primarily in the following characteristics:

1. Plants of the new *Betonica* are more compact and shorter than plants of 'Pink Cotton Candy'.
2. Leaves of plants of the new *Betonica* have darker green-colored leaves than plants of 'Pink Cotton Candy'.
3. Plants of the new *Betonica* have white-colored flowers whereas plants of 'Pink Cotton Candy' have bi-colored light and bright pink-colored flowers.

BRIEF DESCRIPTION OF THE PHOTOGRAPHS

The accompanying colored photographs illustrate the overall appearance of the new *Betonica* plant showing the colors as true as it is reasonably possible to obtain in colored reproductions of this type. Colors in the photographs may differ slightly from the color values cited in the detailed botanical description which accurately describe the colors of the new *Betonica* plant.

The photograph on the first sheet (FIG. 1) is a side perspective view of typical flowering plant of 'Summer Snowcone' grown in a container.

Figure 2:
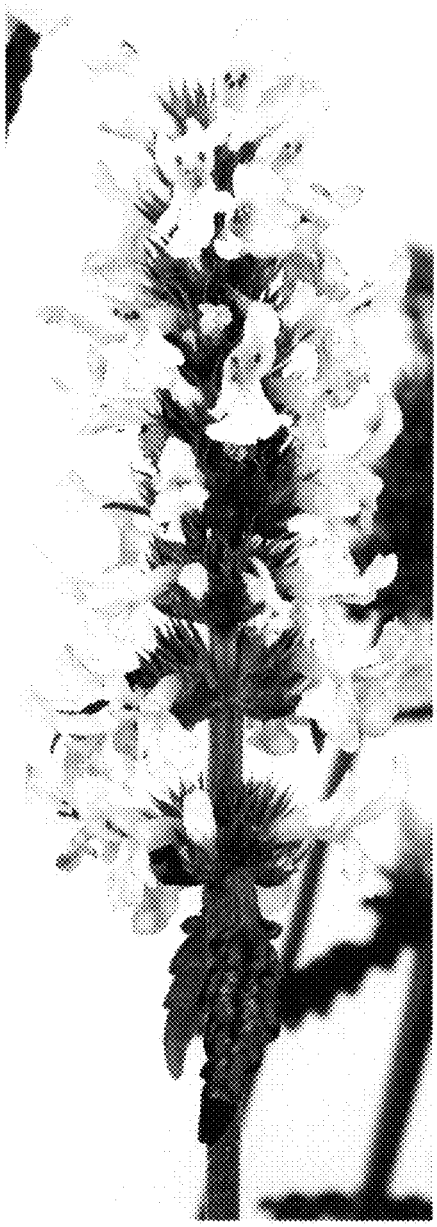

The photograph on the second sheet (FIG. 2) is a close-up view of a typical inflorescence of 'Summer Snowcone'.

DETAILED BOTANICAL DESCRIPTION

The aforementioned photographs and following observations, measurements and values describe plants grown during the summer in 19-cm containers in an outdoor nursery in Lisserbroek, The Netherlands and under cultural practices typical of commercial *Betonica* production. During the production of the plants, day temperatures ranged from 18° C. to 30° C. and night temperatures ranged from 6° C. to 18° C. Plants were one year old when the photographs and description were taken. In the following description, color references are made to The Royal Horticultural Society Colour Chart, 2015 Edition, except where general terms of ordinary dictionary significance are used.

Botanical classification: *Betonica officinalis* 'Summer Snowcone'.

Parentage:

*Female, or seed, parent.*—*Betonica officinalis* 'Alba', not patented.

*Male, or pollen, parent.*—Unknown selection of *Betonica officinalis*, not patented.

Propagation:

*Type.*—By softwood cuttings.

*Time to initiate roots, summer.*—About one month at ambient temperatures about 25° C.

*Time to produce a rooted young plant, summer.*—About three months at ambient temperatures about 20° C.

*Root description.*—Fine to medium in thickness, slightly fibrous; typically greyed white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Herbaceous perennial typically grown as a garden plant; relatively compact and broadly upright plant habit; broadly oblong to broadly obovate in overall plant shape; moderately vigorous to vigorous growth habit; moderate growth rate; freely basal branching habit with about 20 primary basal branches developing per plant.

*Plant height, soil level to top of foliar plane.*—About 33.5 cm.

*Plant height, soil level to top of floral plane.*—About 58.2 cm.

*Plant width* (*spread*).—About 53 cm.

*Basal branches.*—Length: About 17.7 cm. Diameter: About 4.5 mm. Internode length: About 9.8 cm. Shape: Quadrangular. Strength: Strong. Aspect: Upright to slightly outwardly. Texture and luster: Densely pubescent; longitudinally ridged; moderately glossy. Color, developing: Close to 144B. Color, developed: Close slightly darker than 143A; proximally, close to 146C.

Leaf description, basal and cauline leaves:

*Arrangement.*—Opposite, simple.

*Length.*—About 13.5 cm.

*Width.*—About 5.1 cm.

*Shape.*—Narrowly ovate.

*Apex.*—Obtuse to broadly acute.

*Base.*—Truncate to hastate, lobes free to touching.

*Margin.*—Crenate.

*Texture and luster, upper and lower surfaces.*—Densely pubescent, moderately rugose; slightly glossy.

*Venation pattern.*—Pinnate.

*Color.*—Developing leaves, upper surface: Close to 137A. Developing leaves, lower surface: Close to 138A; towards the margins and apex, close to 137B. Fully expanded leaves, upper surface: Close to NN137A; venation, close to 144A. Fully expanded leaves, lower surface: Close to 147B; venation, close to 145C.

*Petioles.*—Length, basal leaves: About 21.6 cm. Length, cauline leaves: About 5.7 cm. Diameter, basal and cauline leaves, flattened: About 3 mm. Texture and luster, basal and cauline leaves, upper and lower surfaces: Moderately pubescent; moderately glossy. Strength, basal and cauline leaves: Strong. Color, basal and cauline leaves, upper and lower surfaces: Close to 144B.

Flower description:

*Flower type, arrangement and habit*.—Single tubular labiate flowers arranged on relatively long terminal racemes; flowers sessile; freely flowering habit with about 160 flowers developing per inflorescence and about 6,200 flowers developing per plant during the flowering season; flowers with an upper lip and a three-lobed lower lip; flowers face mostly outwardly on the raceme.

*Natural flowering season*.—Plants flower for about ten weeks during the summer in The Netherlands.

*Flower longevity on the plant*.—Individual flowers last about one week on the plant; flowers not persistent.

*Fragrance*.—None detected.

*Flower buds*.—Length: About 8 mm. Diameter: About 2 mm. Shape: Oblong. Texture and luster, sepals: Densely pubescent; matte. Texture and luster, petals: Smooth, glabrous; matte. Color, sepals: Close to 137A; proximally, close to 145B. Color, petals: Close to 155C.

*Inflorescence height*.—About 11.9 cm.

*Inflorescence diameter*.—About 3.7 cm.

*Flower diameter*.—About 7 mm by 18 mm.

*Flower length*.—About 1.7 cm.

*Flower throat diameter*.—About 2 mm.

*Flower tube length*.—About 1 cm.

*Flower tube diameter*.—About 2.5 mm.

*Petals*.—Quantity and arrangement: One upper lip and one three-lobed lower lip; lower 60% of the petals are fused into a narrow tube. Length, upper and lower lips, free part: About 7 mm. Width, upper lip: About 3.5 mm. Width, lower lip: About 7 mm. Shape, upper lip: Oblanceolate. Shape, lower lip: Broadly obovate. Apex, upper and lower lips: Obtuse. Margin, upper lip: Entire, not undulate. Margin, lower lip: Entire, moderately undulate. Texture and luster, upper and lower lips, inner surface: Smooth, glabrous, slightly velvety; matte. Texture and luster, upper lip, outer surface: Densely pubescent, slightly velvety; matte. Texture and luster, lower lip, outer surface: Smooth, glabrous, slightly velvety; matte. Texture, throat: Smooth, glabrous. Texture, tube: Densely pubescent. Color, upper lip: When opening and fully opened, inner surface: Close to NN155D. When opening and fully opened, outer surface: Close to NN155D; venation, close to NN155D. Color, lower lip: When opening and fully opened, inner surface: Close to NN155D. When opening and fully opened, outer surface: Close to NN155D; venation, close to 79D. Color, throat: Close to NN155D; venation, close to NN155D. Color, tube: Close to NN155D; venation, close to NN155D.

*Sepals*.—Quantity and arrangement: Five, lower 62.5% fused into a tubular calyx. Calyx length: About 8 mm. Calyx diameter: About 3.5 mm. Length: About 8 mm. Width: About 1.5 mm. Shape: Narrowly oblong. Apex: Narrowly acute. Margin: Entire. Texture and luster, upper surface: Smooth, glabrous; matte. Texture and luster, lower surface: Moderately pubescent; matte. Color: When opening, upper and lower surfaces: Close to 137A; proximally, close to 145B. Fully opened, upper and lower surfaces: Close to 144A; proximally, close to 145B.

*Peduncles*.—Length: About 34.4 cm. Diameter: About 3 mm. Aspect: Mostly upright. Strength: Strong. Texture and luster: Densely pubescent; moderately glossy. Color: Close to 143A.

*Reproductive organs*.—Stamens: Quantity per flower: Four. Filament length: About 2.5 mm to 4 mm. Filament color: Close to NN155D; distally, tinged with close to 76C. Anther shape: Narrowly elliptic; dorsifixed. Anther size: About 0.5 mm by 1 mm. Anther color: Close to 200A. Pollen amount: Scarce. Pollen color: Close to N155A. Pistils: Quantity per flower: One. Pistil length: About 1.1 cm. Stigma diameter: About 1 mm. Stigma shape: Cleft. Stigma color: Close to 76C to 76D. Style length: About 1 cm. Style color: Close to NN155D. Ovary color: Close to 152C to 152D.

*Seeds and fruits*.—To date, seed and fruit production have not been observed on plants of the new *Betonica*.

Pathogen & pest resistance: To date, plants of the new *Betonica* have not been observed to be resistant to pathogens and pests common to *Betonica* plants.

Garden performance: Plants of the new *Betonica* have exhibited good tolerance to rain, wind and temperatures ranging from about −29° C. to 35° C. and to be suitable for USDA Hardiness Zones 4 to 9.

It is claimed:

1. A new and distinct *Betonica* plant named 'Summer Snowcone' as illustrated and described.

* * * * *